United States Patent

Nearn et al.

Patent Number: 5,498,406
Date of Patent: Mar. 12, 1996

[54] TITANIUM DIOXIDE-BASED SUNSCREEN COMPOSITIONS

[76] Inventors: Malcolm R. Nearn, 3 Riverview Road, Kentlyn NSW 2560; Sandra J. Redshaw, 2 Bellevue Avenue, Georges Hall NSW 2198; Graham Burgess, 36 Dowland Street, Bonnyrigg NSW 2177, all of Australia

[21] Appl. No.: 56,050

[22] Filed: Apr. 30, 1993

[51] Int. Cl.$^6$ .............................. A61K 7/42; A61K 7/44; A61K 7/48; A61K 9/12
[52] U.S. Cl. .................................................. 424/59; 424/60
[58] Field of Search .......................... 424/59, 60

[56] References Cited

U.S. PATENT DOCUMENTS

| | | | |
|---|---|---|---|
| 4,820,508 | 4/1989 | Wortzman | 424/59 |
| 4,960,592 | 10/1990 | Hagen et al. | 514/873 |
| 4,997,641 | 3/1991 | Hartnett et al. | 424/70 |
| 5,000,937 | 3/1991 | Grollier et al. | 424/847 |
| 5,028,417 | 7/1991 | Bhat et al. | 514/873 |
| 5,051,250 | 9/1991 | Patel et al. | 424/70 |
| 5,106,613 | 4/1992 | Hartnett et al. | 424/71 |
| 5,116,604 | 5/1992 | Fogel et al. | 514/873 |
| 5,207,998 | 5/1993 | Robinson et al. | 514/873 |
| 5,213,716 | 5/1993 | Patel et al. | 252/546 |
| 5,216,033 | 6/1993 | Pereira et al. | 514/873 |

FOREIGN PATENT DOCUMENTS

| 91/5598 | 3/1993 | South Africa | 424/59 |
|---|---|---|---|

OTHER PUBLICATIONS

Unilin Alcohols (Petrolite Specialty Polymers Group), 1985, Petrolite Corp.

*Primary Examiner*—Shelley A. Dodson
*Assistant Examiner*—Michael A. Williamson
*Attorney, Agent, or Firm*—Martin B. Barancik; Henry S. Goldfine

[57] ABSTRACT

A sunscreen composition in oil-in-water emulsion form comprising cosmetically acceptable oil and water phases and having substantially uniformly suspended therein from about 1% to about 5%, by weight, of microfine $TiO_2$ having a particle size of less than about 100 nm, the composition further comprising a dispersing agent in an amount sufficient to stabilize the emulsion, the dispersing agent comprising a member selected from the group consisting of a long chain saturated primary alcohol, a derivative thereof or a mixture thereof, the member having an average of from about 25 to about 45 carbon atoms in the long chain.

7 Claims, No Drawings

TITANIUM DIOXIDE-BASED SUNSCREEN COMPOSITIONS

BACKGROUND OF THE INVENTION

1. Field of the Invention

The present invention relates to novel titanium dioxide sunscreen compositions.

2. Description of the Prior Art

Sunscreen compositions are commonly used during outdoor work or leisure for protection of exposed skin against painful sunburn. Many effective sunscreen preparations are sold commercially or are described in the cosmetic or pharmaceutical literature. In general, sunscreen preparations are formulated in the form of a cream, lotion or oil containing as the active agent an ultraviolet radiation absorbing chemical compound. The active agent acts to block the passage of erythematogenic radiation, thereby preventing its penetration into the skin.

The ideal sunscreen formulation should be nontoxic and non-irritating to skin tissue and be capable of convenient application to the skin in a uniform continuous film. The product should be sufficiently stable chemically and physically so as to provide an acceptable shelf life upon storage. It is particularly desirable that the preparation should retain its protective effect over a prolonged period after application. Thus, the active agent when present on the skin must be resistant to chemical or photo-degradation, to absorption through the skin and to removal by perspiration, skin oil or water. For aesthetic reasons, the product should be substantially odorless (or be capable of being scented) and be non-staining to the skin or clothing.

Microfine titanium dioxide has been found to be an effective sunscreen agent (U.S. Pat. Nos. 5,188,831 and 5,028,417; Japanese Patent Application No. 81-161,881; European Patent Application No. 91 30 40 98.6 published Nov. 13, 1991; Japanese Patent Publication No. 60-231,607; and British Journal of Dermatology, p. 275 (1971)) in that, when employed in cosmetic formulations in sufficiently small particle sizes, it is capable of transmitting visible light, but reflects and scatters harmful ultraviolet rays.

Relatively large amounts of microfine $TiO_2$ can readily be incorporated into water-in-oil emulsions; however, such emulsions tend to feel greasier and are generally less acceptable cosmetically than oil-in-water emulsions. On the other hand, it has been difficult heretofore to form stable oil-in-water emulsions containing more than about 1%, by weight, of microfine $TiO_2$. The presence of such low levels of microfine titanium dioxide does not increase the sunscreen protection.

It is an object of the present invention to provide stable oil-in-water emulsion compositions containing sufficiently large amounts of microfine $TiO_2$ to increase sunscreen protection.

SUMMARY OF THE INVENTION

The present invention provides stable compositions which combine the superior cosmetic properties of oil-in-water emulsions with the desirable sunscreen characteristics of microfine $TiO_2$.

This and other objects are realized by the present invention, one embodiment of which is a sunscreen composition in oil-in-water emulsion form comprising cosmetically acceptable properties and having substantially uniformly suspended therein from about 1% to about 5%, by weight, of microfine $TiO_2$ having a mean particle size of less than about 100 nm, the composition further comprising a dispersing agent in an amount sufficient to stabilize the emulsion, the dispersing agent comprising a member selected from the group consisting of a long chain saturated primary alcohol, a derivative thereof or a mixture thereof, the member having an average of from about 25 to about 45 carbon atoms in the long chain.

DETAILED DESCRIPTION OF THE INVENTION

In a preferred embodiment of the invention, microfine $TiO_2$ having a particle size in the range of from about 5 to about 100 nm, most preferably from about 10 to about 25 nm, is utilized in the preparation of the sunscreen compositions. Microfine $TiO_2$ having the requisite particle sizes are prepared according to well-known commercial methods, such as the method described in Australian Patent No. 599,229. The titanium dioxide is usually surface-treated (e.g., with aluminum stearate) to prevent graying in sunlight.

The present invention is predicated on the discovery that certain long chain saturated primary alcohols or derivatives thereof function to stabilize oil-in-water emulsions containing relatively large amounts of microfine $TiO_2$ over long periods of time.

Suitable such alcohols are long chain saturated primary alcohols or derivatives thereof having an average of from about 25 to about 45 carbon atoms in the long chain. The stabilizing agent generally comprises a mixture of homologous alcohols, all typically having an even number of carbon atoms in the long chain, averaging 24 to 45 carbon atoms.

The long chain primary alcohols of the compositions of this invention are preferably saturated compounds, with the hydroxy group being terminally located. Such alcohols will normally be of a distribution of homologous alcohols and typically all are of even numbers of carbon atoms, averaging 24 to 45 carbon atoms (on a weight basis), preferably 28 to 42 carbon atoms, more preferably about 30 to about 40 carbon atoms and most preferably 30 to 40 carbon atoms. When the average number of carbon atoms in the chain is less than 24, the desired effectiveness of such alcohols in the present formulations is decreased, and when such chain length is more than 45 carbon atoms, e.g., of an average of about 50 carbon atoms, such alcohols are not satisfactorily dispersible in the described compositions. In addition to the mentioned long chain alcohols, related compounds such as corresponding alkoxylated alcohols, corresponding fatty acids and long chain saturated primary alcohol esters may be substituted, at least in part. Of such "derivatives," the alkoxylated alcohols are preferred, and the most preferred of these are the ethoxylated alcohols, which will normally contain up to about 20 ethoxy groups per mole, e.g., about 10 to 20. However, the alcohols which are the preferred embodiment of the invention normally will be employed alone or in mixture with related compounds from the "derivatives" group, with the alcohol being the major proportion of the total "alcohol plus derivatives" content. Examples of commercial materials which may be employed in the present compositions are those manufactured by Petrolite Corporation and sold through their Petrolite Specialty Polymers Group under the name Unilin™ Alcohols, as described in the technical bulletin entitled Unilin™ Alcohols, copyrighted in 1985 and identified as SP-1040. Such alcohols may be 75 to 90%, e.g., 80 to 85%, of the commercial product, with the balance of such products being substantially all saturated hydrocarbons of corresponding chain lengths. In such products, the distribution curve for the alcohol is substantially bell-shaped, with no chain length of alcohol being more than 10% of the total content thereof, and with the corresponding hydrocarbon content being of a substantially flat distribution curve, with about 1 or 2% of each of the hydrocarbons being present. Such distribution curves, as bar graphs, are given in the Petrolite Bulletin mentioned hereinabove. The alcohols (and corresponding hydrocarbons) present will normally be of chain lengths such that at least 80% are in the range of 18 or 20 to 54 carbon atoms, with at least 80% being in the range of about 18 or 20 to 44 carbon atoms for an alcohol averaging about 30 carbon atoms. and with at least 80% being in the range of about 28 or 30 to 54 carbon atoms when the alcohol averages about 40 carbon atoms. Examples of the long chain primary alcohols are Unilin-425 alcohol which averages 40 carbon atoms in its chain, and Unilin-350 which averages about 26 carbon atoms in its chain. A derivative, Unithox-550, is an ethoxylated such alcohol of an average of 40 carbon atoms in the alkyl chain, ethoxylated with up to 20 ethoxy groups, e.g., 13.

The alcohol or derivative is employed in the compositions of the invention in amounts sufficient to stabilize the oil-in-water emulsion and to render it cosmetically acceptable. Generally, an amount of alcohol or derivative in the range of from about 0.2% to about 10%, most preferably from about 0.5% to about 5%, by weight [all percentages expressed herein are by weight based on the total weight of the composition in which the described ingredient appears, unless indicated otherwise] is sufficient to stabilize typical oil-in-water cosmetic emulsions containing an amount of microfine $TiO_2$ within the above-described ranges. Given the description of the invention herein, it will be well within the skill of the art to determine, for a particular oil-in-water emulsion containing microfine $TiO_2$, the amount of long chain alcohol or derivative necessary to achieve an acceptable level of stability.

It will further be understood by those skilled in the art that the oil-in-water emulsion compositions of the invention may be formulated in any desirable form such as solid, liquid or aerosol, e.g., lotions, creams, facial cosmetics and the like.

It will additionally be understood by those skilled in the art that other sunscreen agents and cosmetic adjuvants compatible with the components of the composition of the invention may also be incorporated therein. Exemplary of such co-ingredients are:

Octyl dimethyl PABA (sunscreen)
Octyl salicylate (sunscreen)
Octocrylene (sunscreen)
Phenoxyethanol (preservative)
Germall II (preservative)
Parabens (preservative)
Benzyl alcohol (preservative)
Imidazolidinyl urea (preservative)
Fatty esters (emollient)
Vegetable oils (emollient)
Mineral oils (emollient)
Glycerol (moisturizer)
Cetostearyl alcohol (stabilizer)
Propylene glycol (moisturizer)
Carbomers (thickener)
Isostearic acid (emulsifier)
Stearic acid (emulsifier)
Arlacel 165 (emulsifier)
Amphisol K (emulsifier)
Xanthan gum (thickener)
Disodium EDTA (chelates metal ions)
Silicone oil (emollient, water-proofing)
Petrolatum (emollient)
Carnauba wax (stabilizer)
Ammonia (neutralize acids and Carbomer)
Fragrance The oil-in-water emulsions of the invention are generally prepared according to the following procedure:

1. Mix thickeners and add to water in which disodium EDTA has been dissolved. Add ammonia until the pH lies between pH 8.0 and 9.0. Heat to 80°–85° C.

2. Combine oil phase ingredients [sunscreens, stearic acid, silicone oil, cetostearyl alcohol, petrolatum, mineral oil, carnauba wax, glyceryl stearate, PEG-100 stearate, and Solsperse (if used)] and heat to 80°–85° C.

3. Mix isostearic acid, isopropyl palmitate and microfine titanium dioxide to a smooth paste; add to above mixture 2 and heat the mixture to 80°–85° C.

4. Add mixtures 2 and 3 to mixture 1 and homogenize.

5. Cool to 40°–45° C.; then add preservative and perfume, if required.

Oil-in-water emulsions containing as little as 1%, by weight, of microfine $TiO_2$ have been found to be stable for at least two years at 40° C. and for more than a month at 55° C. As noted above, however, the inclusion of such small amounts of microfine $TiO_2$ does not substantially contribute to sunscreen protection. Similar formulations containing 2% and 5%, by weight, of microfine $TiO_2$ were found to destabilize, i.e., separate into discrete phases, after only one month at 55° C.

Specific embodiments of the invention are illustrated by the following non-limiting examples.

EXAMPLE 1

The formulations set forth in Tables 1 and 2 were prepared according to the following procedure.

Carbomer 941 and Keltrol F (xanthan gum) were mixed and added to water in which disodium EDTA was dissolved. Ammonia (12.5%) was added until the pH was between pH 8.0 and 9.0 and the mixture was heated to 80°–85° C.

The oil phase ingredients were combined: paraffin soft white, phenyl trimethicone, light liquid paraffin, carnauba wax, cetostearyl alcohol, sunscreen actives, glyceryl stearate/PEG-100 stearate (Arlacel 165), stearic acid and optionally Solsperse 3000 or 6000. The mixture was then heated to 80°–85° C.

Isostearic acid, isopropyl palmitate and microfine titanium dioxide were mixed to a smooth paste and added to the heated oil phase, and the mixture was heated to 80°–85° C.

The heated oil phase was added to the heated water phase and the resulting mixture was homogenized.

The product was cooled to 40°–45° C., and preservatives and fragrance were added. The mixing of the formulation was continued until the temperature reached 35°–40° C.

The functions of the various components of the formulation are as follows:

| Component | Function |
|---|---|
| Water | diluent |
| Xanthan Gum | thickener |
| Carbomer 941 | thickener |
| Disodium EDTA | chelating agent |
| Ammonia (12.5%) | neutralizer |
| Isopropyl Palmitate | emollient |
| Paraffin Soft White | emollient |
| Phenyl Trimethicone | water resistance |
| Isostearic Acid | emulsifier |
| Light Liquid Paraffin | emollient |
| Carnauba Wax | stabilizer |

-continued

| Component | Function |
|---|---|
| Cetostearyl Alcohol | stabilizer |
| Octyl Methoxycinnamate | sunscreen |
| Octyl Salicylate | sunscreen |
| $TiO_2$ | sunscreen |
| Oxybenzone | sunscreen |
| Glyceryl Stearate/PEG-100 Stearate | emulsifier |
| Stearic Acid | emulsifier |
| Solsperse 3000 | dispersant |
| Solsperse 6000 | dispersant |
| Phenoxyethanol/Parabens | preservative |
| Fragrance | fragrance |

TABLE 1

| | Percentages By Weight | | | | | |
|---|---|---|---|---|---|---|
| Raw Materials | A | B | C | D | E | F |
| Water | 64.93 | 64.93 | 68.93 | 68.93 | 65.43 | 65.43 |
| Xanthan Gum | 0.1 | 0.1 | 0.1 | 0.1 | 0.1 | 0.1 |
| Carbomer 941 | 0.3 | 0.3 | 0.3 | 0.3 | 0.3 | 0.3 |
| EDTA (Disodium salt) | 0.02 | 0.02 | 0.02 | 0.02 | 0.02 | 0.02 |
| Ammonia (12.5%) | 0.6 | 0.6 | 0.6 | 0.6 | 0.6 | 0.6 |
| Isopropyl Palmitate | 3.0 | 3.0 | 3.0 | 3.0 | 3.0 | 3.0 |
| Paraffin Soft White | 2.0 | 2.0 | 2.0 | 2.0 | 2.0 | 2.0 |
| Phenyl Trimethicone | 2.0 | 2.0 | 2.0 | 2.0 | 2.0 | 2.0 |
| Isostearic Acid | 2.0 | 2.0 | 2.0 | 2.0 | 2.0 | 2.0 |
| Light Liquid Paraffin | 1.0 | 1.0 | 1.0 | 1.0 | 1.0 | 1.0 |
| Carnauba Wax | 1.0 | 1.0 | 1.0 | 1.0 | 1.0 | 1.0 |
| Cetostearyl Alcohol | 0.5 | 0.5 | 0.5 | 0.5 | 0.5 | 0.5 |
| Octyl Methoxycinnamate | 9.0 | 9.0 | 10.0 | 10.0 | 9.0 | 9.0 |
| Octyl Salicylate | 5.0 | 5.0 | — | — | — | — |
| $TiO_2$ | 5.0 | 5.0 | 5.0 | 5.0 | 2.0 | 2.0 |
| Oxybenzone | — | — | — | — | 2.5 | 2.5 |
| Glyceryl Stearate/ PEG-100 Stearate | 1.0 | 1.0 | 1.0 | 1.0 | 1.0 | 1.0 |
| Stearic Acid | 0.5 | 0.5 | 0.5 | 0.5 | 0.5 | 0.5 |
| Solsperse 3000 | 1.0 | — | 1.0 | — | 1.0 | — |
| Solsperse 6000 | — | 1.0 | — | 1.0 | — | 1.0 |
| Phenoxyethanol/Parabens | 0.8 | 0.8 | 0.8 | 0.8 | 0.8 | 0.8 |
| Fragrance | 0.25 | 0.25 | 0.25 | 0.25 | 0.25 | 0.25 |
| | 100.0 | 100.0 | 100.0 | 100.0 | 100.0 | 100.0 |

Solsperse 3000 - $H(OCH.C_6H_{13}(CH_2)_{10}CO)_6OH$
Solsperse 6000 - $H((OCH.C_6H_{13}(CH_2)_{10}C)_nO)_2Ca^{2+}$ [n = 5 - 6]

TABLE 2

| | Percentages By Weight | | | | | | | |
|---|---|---|---|---|---|---|---|---|
| Raw Materials | A | B | C | D | E | F | G | H |
| Water | 66.93 | 69.43 | 70.93 | 70.93 | 66.68 | 66.43 | 71.43 | 66.96 |
| Xanthan Gum | 0.1 | 0.1 | 0.1 | 0.1 | 0.1 | 0.1 | 0.1 | 0.1 |
| Carbomer 941 | 0.3 | 0.3 | 0.3 | 0.3 | 0.3 | 0.3 | 0.3 | 0.3 |
| EDTA (Disodium salt) | 0.02 | 0.02 | 0.02 | 0.02 | 0.02 | 0.02 | 0.02 | 0.02 |
| Ammonia (12.5%) | 0.6 | 0.6 | 0.6 | 0.6 | 0.6 | 0.6 | 0.6 | 0.6 |
| Propylene Glycol | — | — | — | — | 3.0 | — | — | 3.0 |
| Isopropyl Palmitate | 3.0 | 3.0 | 3.0 | 3.0 | 3.0 | 3.0 | 3.0 | 3.0 |
| Paraffin Soft White | 2.0 | 2.0 | 2.0 | 2.0 | 2.0 | 2.0 | 2.0 | 2.0 |
| Phenyl Trimethicone | 2.0 | 2.0 | 2.0 | 2.0 | 2.0 | 2.0 | 2.0 | 2.0 |
| Isostearic Acid | 2.0 | 2.0 | 2.0 | 2.0 | 2.0 | 2.0 | 2.0 | 2.0 |
| Light Liquid Paraffin | 1.0 | 1.0 | 1.0 | 1.0 | 1.0 | 1.0 | 1.0 | 1.0 |
| Carnauba wax | 1.0 | 1.0 | 1.0 | 1.0 | 1.0 | 1.0 | 1.0 | — |
| Cetostearyl Alcohol | 0.5 | 0.5 | 0.5 | 0.5 | 0.5 | 0.5 | 0.5 | 0.5 |
| Octyl Methoxycinnamate | 9.0 | 10.0 | 9.0 | 9.0 | — | 9.0 | 9.0 | — |
| Octyl Salicylate | 5.0 | — | — | — | — | 5.0 | — | — |
| $TiO_2$ | 4.0 | 5.0 | 2.0 | 2.0 | — | 4.0 | 2.0 | — |
| Eusolex 4360 | — | — | 2.5 | 2.5 | — | — | 2.5 | — |
| Glyceryl Stearate/PEG-100 Stearate | 1.0 | 1.0 | 1.0 | 1.0 | 1.0 | 1.0 | 1.0 | 1.0 |
| Stearic Acid | 0.5 | 0.5 | 0.5 | 0.5 | 0.5 | 0.5 | 0.5 | 0.5 |
| $TiO_2$ Premix | — | — | — | — | 14.07 | — | — | 14.07 |

TABLE 2-continued

| Raw Materials | Percentages By Weight | | | | | | | |
|---|---|---|---|---|---|---|---|---|
| | A | B | C | D | E | F | G | H |
| Solsperse 6000 | — | — | — | 0.5 | 1.0 | — | — | — |
| Solsperse 20000 | — | 0.5 | 0.5 | — | — | 0.5 | — | 1.0 |
| Polyethylene 617 | — | — | — | — | — | — | — | 0.9 |
| Phenoxyethanol/Parabens | 0.8 | 0.8 | 0.8 | 0.8 | 0.8 | 0.8 | 0.8 | 0.8 |
| Fragrance | 0.25 | 0.25 | 0.25 | 0.25 | 0.25 | 0.25 | 0.25 | 0.25 |
| | 100.0 | 100.0 | 100.0 | 100.0 | 100.0 | 100.0 | 100.0 | 100.0 |

Solsperse 20000 - $(C_2H_5)_2N(CH_2CH_2O)_{11}(CH_2CH.CH_3.O)_{20}H$

Solsperse 3000, Solsperse 6000, Solsperse 20000 (polyalkylene oxide condensates) and stearic acid are known stabilizers for titanium dioxide dispersions. Their presence in the formulations described in Tables 1 and 2, all of which contain 2% or more $TiO_2$, however, did not stabilize the emulsions. All were found to have destabilized after one month at 55° C.

EXAMPLE 2

The formulations set forth in Table 3 were prepared according to the following procedure.

Carbomer 941 and Keltrol F (xanthan gum) were mixed and added to water in which phenylbenzimidazole sulfonic acid, triethanolamine, glycerine and PPG-20 methyl glucose ether distearate were dissolved. The mixture was heated to 80°–85° C.

The oil phase ingredients were combined: paraffin soft white, phenyl trimethicone, Unilin, light liquid paraffin, cetostearyl alcohol, sunscreen actives, glyceryl stearate/PEG-100 stearate (Arlacel 165), propylparaben stearic acid and 12-hydroxystearic acid (if used). The mixture was then heated to 80°–85° C.

The isopropyl palmitate and microfine titanium dioxide were mixed to a smooth paste and added to the heated oil phase. Potassium cetyl phosphate was added to the heated oil phase and dissolved. The oil phase was then reheated to 80°–85° C.

The heated oil phase was added to the heated water phase and homogenized.

The resulting mixture was cooled to 40°–45° C., and preservatives and fragrance (if required) were added.

TABLE 3

| Raw Materials | Percentages By Weight | | | | |
|---|---|---|---|---|---|
| | A | B | C | D | E |
| Water | 74.8 | 74.7 | 74.2 | 74.8 | 73.2 |
| Xanthan Gum | 0.1 | 0.1 | 0.1 | 0.1 | 0.1 |
| Carbomer 941 | 0.2 | 0.3 | 0.3 | 0.2 | 0.3 |
| Triethanolamine | 1.5 | 1.5 | 1.5 | 1.5 | 1.5 |
| Glycerine | 0.5 | 0.5 | 0.5 | 0.5 | 0.5 |
| PPG-20 Methyl Glucose Ether Distearate | 2.0 | 2.0 | 2.0 | 2.0 | 2.0 |
| Potassium Cetyl Phosphate | 1.0 | 1.0 | 1.0 | 1.0 | 1.0 |
| Phenylbenzimidazole Sulfonic Acid | 2.0 | 2.0 | 2.0 | 2.0 | — |
| Octyl Methoxycinnamate | 6.0 | 6.0 | 6.0 | 6.0 | 7.5 |
| $TiO_2$ | 2.0 | 2.0 | 2.0 | 2.0 | 2.0 |
| Oxybenzone | — | — | — | — | 1.5 |
| Isopropyl Palmitate | 3.0 | 3.0 | 3.0 | 3.0 | 3.0 |
| Paraffin Soft White | 1.0 | 1.0 | 1.0 | 1.0 | 1.0 |
| Phenyl Trimethicone | 2.0 | 2.0 | 2.0 | 2.0 | 2.0 |
| Light Liquid Paraffin | 1.0 | 1.0 | 1.0 | 1.0 | 1.0 |
| Unilin | 1.0 | 1.0 | 1.0 | 0.5 | 1.0 |
| Cetostearyl Alcohol | 0.5 | 0.5 | 0.5 | 0.5 | 0.5 |
| Glyceryl Stearate/PEG-100 Stearate | 0.5 | 0.5 | 0.5 | 0.5 | 0.5 |
| Stearic Acid | 0.5 | 0.5 | 0.5 | 0.5 | 0.5 |
| 12-Hydroxystearic Acid | — | — | 0.5 | 0.5 | 0.5 |
| Propylparaben | 0.05 | 0.05 | 0.05 | 0.05 | 0.05 |
| Imidazolidinyl Urea | 0.2 | 0.2 | 0.2 | 0.2 | 0.2 |
| Methylparaben | 0.15 | 0.15 | 0.15 | 0.15 | 0.15 |
| | 100.0 | 100.0 | 100.0 | 100.0 | 100.0 |

Each of the compositions in Table 3 remained stable after one month at 55° C.

EXAMPLE 3

The emulsions set forth in Table 4 were formulated according to the following procedure.

Carbomer 941 and Keltrol F (xanthan gum) were mixed and added to water in which disodium EDTA was dissolved. Ammonia (12.5%) was added until the pH was between pH 8.0 and 9.0, and the mixture was heated to 80°–85° C.

The oil phase ingredients were combined: paraffin soft white, phenyl trimethicone, light liquid paraffin, carnauba wax, cetostearyl alcohol, sunscreen actives, glyceryl stearate/PEG-100 stearate (Arlacel 165), Unilin and stearic acid. The mixture was then heated to 80°–85° C.

Isostearic acid, isopropyl palmitate and microfine titanium dioxide were mixed to a smooth paste and added to the heated oil phase. The mixture was then heated to 80°–85° C.

The heated oil phase was added to the heated water phase. Preservative was added and the mixture was homogenized and cooled to 40°–45° C. Fragrance was then added (if required).

TABLE 4

| Raw Materials | Percentages By Weight | | | | | |
|---|---|---|---|---|---|---|
| | A | B | C | D | E | F |
| Water | 61.43 | 63.43 | 65.43 | 66.43 | 66.43 | 68.93 |
| Xanthan Gum | 0.1 | 0.1 | 0.1 | 0.1 | 0.1 | 0.1 |
| Carbomer 941 | 0.3 | 0.3 | 0.3 | 0.3 | 0.3 | 0.3 |
| EDTA (Disodium salt) | 0.02 | 0.02 | 0.02 | 0.02 | 0.02 | 0.02 |
| Ammonia (12.5%) | 0.6 | 0.6 | 0.6 | 0.6 | 0.6 | 0.6 |
| Isopropyl Palmitate | 3.0 | 3.0 | 3.0 | 3.0 | 3.0 | 3.0 |
| Paraffin Soft White | 2.0 | 2.0 | 2.0 | 2.0 | 2.0 | 2.0 |
| Phenyl Trimethicone | 2.0 | 2.0 | 2.0 | 2.0 | 2.0 | 2.0 |
| Isostearic Acid | 2.0 | 2.0 | 2.0 | 2.0 | 2.0 | 2.0 |
| Light Liquid Paraffin | 1.0 | 1.0 | 1.0 | 1.0 | 1.0 | 1.0 |
| Carnauba Wax | 1.0 | 1.0 | 1.0 | 1.0 | 1.0 | 1.0 |
| Cetostearyl Alcohol | 0.5 | 0.5 | 0.5 | 0.5 | 0.5 | 0.5 |
| Octyl Methoxycinnamate | 9.0 | 9.0 | 9.0 | 9.0 | 9.0 | 9.0 |
| Glyceryl Stearate/ PEG-100 Stearate | 1.0 | 1.0 | 1.0 | 1.0 | 1.0 | 1.0 |
| Oxybenzone | 2.5 | 2.5 | 2.5 | 2.5 | — | 2.5 |
| $TiO_2$ | 7.0 | 5.0 | 3.0 | 2.0 | 5.0 | 5.0 |
| Stearic Acid (Triple Pressed) | 0.5 | 0.5 | 0.5 | 0.5 | 0.5 | 0.5 |
| Fragrance | 0.25 | 0.25 | 0.25 | 0.25 | 0.25 | 0.25 |
| Phenoxyethanol/Parabens | 0.8 | 0.8 | 0.8 | 0.8 | 0.8 | 0.8 |
| Unilin | 5.0 | 5.0 | 5.0 | 2.0 | 2.0 | 2.0 |
| | 100.0 | 100.0 | 100.0 | 100.0 | 100.0 | 100.0 |

Each of the formulations in Table 4 were found to retain a high degree of stability after two weeks at 55° C.

EXAMPLE 4

The compositions of Table 5 were prepared according to the following method.

Carbomer 941 and Keltrol F (xanthan gum) were added to water in which disodium EDTA was dissolved. Ammonia (12.5%) was added until the pH was between pH 8.0 and 9.0. The mixture was then heated to 80°–85° C.

The oil phase ingredients were combined: paraffin soft white, phenyl trimethicone, light liquid paraffin, carnauba wax, cetostearyl alcohol, sunscreen actives, glyceryl stearate/PEG-100 stearate (Arlacel 165), Unilin and stearic acid. The mixture was then heated to 80°–85° C.

Isostearic acid, isopropyl palmitate and microfine titanium dioxide were mixed to a smooth paste and added to the heated oil phase. The mixture was then heated to 80°–85° C.

The heated oil phase was added to the heated water phase. Preservative was added and the mixture was homogenized and cooled to 40°–45° C. Fragrance was then added (if required).

TABLE 5

| Raw Materials | Percentages By Weight | | | | |
|---|---|---|---|---|---|
| | A | 6 | C | D | E |
| Water | 71.43 | 70.43 | 65.43 | 60.43 | 61.93 |
| Xanthan Gum | 0.1 | 0.1 | 0.1 | 0.1 | 0.1 |
| Carbomer 941 | 0.3 | 0.3 | 0.3 | 0.3 | 0.3 |
| EDTA (Disodium salt) | 0.02 | 0.02 | 0.02 | 0.02 | 0.02 |
| Ammonia (12.5%) | 0.6 | 0.6 | 0.6 | 0.6 | 0.6 |
| Isopropyl Palmitate | 3.0 | 3.0 | 3.0 | 3.0 | 3.0 |
| Paraffin Soft White | 2.0 | 2.0 | 2.0 | 2.0 | 2.0 |
| Phenyl Trimethicone | 2.0 | 2.0 | 2.0 | 2.0 | 2.0 |
| Isostearic Acid | 2.0 | 2.0 | 2.0 | 2.0 | 2.0 |
| Light Liquid Paraffin | 1.0 | 1.0 | 1.0 | 1.0 | 1.0 |
| Carnauba Wax | 1.0 | 1.0 | 1.0 | 0.5 | 1.0 |
| Cetostearyl Alcohol | 0.5 | 0.5 | 0.5 | 0.5 | 0.5 |
| Octyl Methoxycinnamate | 9.0 | 9.0 | 9.0 | 9.0 | 9.0 |
| Glyceryl Stearate/PEG-100 Stearate | 1.0 | 1.0 | 1.0 | 0.5 | 1.0 |
| Oxybenzone | 2.5 | 2.5 | 2.5 | 2.5 | 2.5 |
| $TiO_2$ | 2.0 | 2.0 | 5.0 | 10.0 | 7.5 |
| Stearic Acid | 0.5 | 0.5 | 0.5 | 0.5 | 0.5 |
| Phenoxyethanol/Parabens | 0.8 | 0.8 | 0.8 | 0.8 | 0.8 |
| Fragrance | 0.25 | 0.25 | 0.25 | 0.25 | 0.25 |
| Unilin 425 | — | 1.0 | 3.0 | 5.0 | 4.0 |
| | 100.0 | 100.0 | 100.0 | 100.0 | 100.0 |

Formulation A, containing no long chain alcohol stabilizers, began to separate after only two weeks at 55° C. The remainder of the formulations, each containing a long chain alcohol stabilizer, remained stable after one month at 55° C.

EXAMPLE 5

The composition set forth in Table 6 was formulated according to the following procedure.

Carbomer 941 and Keltrol F (xanthan gum) were added to water in which phenylbenzimidazole sulfonic acid, triethanolamine, glycerine and PPG-20 methyl glucose ether distearate were dissolved. Methylparaben and imidazolidinyl urea were added and the mixture was heated to 80°–85° C.

The oil phase ingredients were combined: paraffin soft white, phenyl trimethicone, Unilin, light liquid paraffin, cetostearyl alcohol, sunscreen actives, glyceryl stearate/PEG-100 stearate (Arlacel 165), propylparaben and stearic acid. The mixture was then heated to 80°–85° C.

Isopropyl palmitate and microfine titanium dioxide were mixed to a smooth paste and added to the heated oil phase. Potassium cetyl phosphate was added to the heated oil phase and dissolved. The oil phase was then reheated to 80°–85° C.

The heated oil phase was added to the heated water phase and the mixture was homogenized and cooled to 40°–45° C. Fragrance was then added.

TABLE 6

| Raw Materials | Weight % |
| --- | --- |
| Water | 74.6 |
| Xanthan Gum | 0.1 |
| Carbomer 941 | 0.3 |
| Triethanolamine | 1.6 |
| Glycerine | 0.5 |
| PPG-20 Methyl Glucose Ether Distearate | 2.0 |
| Potassium Cetyl Phosphate | 1.0 |
| Phenylbenzimidazole Sulfonic Acid | 2.0 |
| Octyl Methoxycinnamate | 6.0 |
| TiO$_2$ | 2.0 |
| Isopropyl Palmitate | 3.0 |
| Paraffin Soft White | 1.0 |
| Phenyl Trimethicone | 2.0 |
| Light Liquid Paraffin | 1.0 |
| Unilin | 1.0 |
| Cetostearyl Alcohol | 0.5 |
| Glyceryl Stearate/PEG-100 Stearate | 0.5 |
| Stearic Acid | 0.5 |
| Propylparaben | 0.05 |
| Imidazolidinyl Urea | 0.2 |
| Methylparaben | 0.15 |
| | 100.0 |

The oil-in-water emulsion of Table 6 remained stable after three months at 4° C., 30° C., 40° C. and 50° C.

EXAMPLE 6

The emulsions of Table 7 were prepared according to the following method.

Carbomer 941 and Keltrol F (xanthan gum) were mixed and added to water in which phenylbenzimidazole sulfonic acid, triethanolamine, glycerine and PPG-20 methyl glucose ether distearate were dissolved. Methylparaben and imidazolidinyl urea were added and the mixture was heated to 80°–85° C.

The oil phase ingredients were combined: paraffin soft white, phenyl trimethicone, Unilin, light liquid paraffin, cetostearyl alcohol, sunscreen actives, glyceryl stearate/PEG-100 stearate (Arlacel 165), propyl paraben, stearic acid and 12-hydroxystearic acid (if used). The mixture was then heated to 80°–85° C.

Isopropyl palmitate and microfine titanium dioxide were mixed to a smooth paste and added to the heated oil phase. Potassium cetyl phosphate was added to the heated oil phase and dissolved. The oil phase was then reheated to 80°–85° C.

The heated oil phase was added to the heated water phase and the mixture was homogenized and cooled to 40°–45° C. Fragrance was added (if required).

TABLE 7

| | Percentages By Weight | | |
| --- | --- | --- | --- |
| Raw Materials | A | B | C | D |
| Water | 74.2 | | 74.7 | 75.2 |
| Xanthan Gum | 0.1 | | 0.1 | 0.1 |
| Carbomer 941 | 0.3 | | 0.3 | 0.3 |
| Triethanolamine | 1.5 | | 1.5 | 1.5 |
| Glycerine | 0.5 | | 0.5 | 0.5 |
| PPG-20 Methyl Glucose Ether Distearate | 2.0 | | 2.0 | 2.0 |
| Potassium Cetyl Phosphate | 1.0 | | 1.0 | 1.0 |
| Phenylbenzimidazole Sulfonic Acid | 2.0 | | 2.0 | 2.0 |
| Octyl Methoxycinnamate | 6.0 | | 6.0 | 6.0 |
| TiO$_2$ | 2.0 | | 2.0 | 2.0 |
| Isopropyl Palmitate | 3.0 | | 3.0 | 3.0 |
| Paraffin Soft White | 1.0 | | 1.0 | 1.0 |
| Phenyl Trimethicone | 2.0 | | 2.0 | 2.0 |
| Light Liquid Paraffin | 1.0 | | 1.0 | 1.0 |
| Unilin | 1.0 | | 1.0 | 1.5 |
| Cetostearyl Alcohol | 0.5 | | 0.5 | — |
| Glyceryl Stearate/PEG-100 Stearate | 0.5 | | 0.5 | — |
| Stearic Acid | 0.5 | | 0.5 | 0.5 |
| 12-Hydroxystearic Acid | 0.5 | | — | — |
| Propylparaben | 0.05 | | 0.05 | 0.05 |
| Imidazolidinyl Urea | 0.2 | | 0.2 | 0.2 |
| Methylparaben | 0.15 | | 0.15 | 0.15 |
| | 100.0 | | 100.0 | 100.0 |

Each of the compositions in Table 7 remained stable after two weeks at 55° C.

EXAMPLE 7

The emulsion of Table 8 was prepared according to the following method.

Carbomer 941 and Keltrol F (xanthan gum) were mixed and added to water in which phenylbenzimidazole sulfonic acid, triethanolamine, glycerine and PPG-20 methyl glucose ether distearate were dissolved. Methylparaben and imidazolidinyl urea were added and the mixture was heated to 80°–85° C.

The oil phase ingredients were combined: paraffin soft white, phenyl trimethicone, Unilin, light liquid paraffin, cetostearyl alcohol, sunscreen actives, glyceryl stearate/PEG-100 stearate (Arlacel 165), propylparaben and stearic acid. The mixture was then heated to 80°–85° C.

Isopropyl palmitate and microfine titanium dioxide were mixed to a smooth paste and added to the heated oil phase. Potassium cetyl phosphate was added to the heated oil phase and dissolved. The oil phase was then reheated to 80°–85° C.

The heated oil phase was added to the heated water phase and the mixture was homogenized and cooled to 40°–45° C. Fragrance was added (if required).

TABLE 8

| Raw Materials | Weight % |
| --- | --- |
| Water | 75.3 |
| Xanthan Gum | 0.1 |
| Carbomer 941 | 0.2 |
| Triethanolamine | 1.5 |
| Glycerine | 0.5 |
| PPG-20 Methyl Glucose Ether Distearate | 2.0 |
| Potassium Cetyl Phosphate | 1.0 |
| Phenylbenzimidazole Sulfonic Acid | 2.0 |
| Octyl Methoxycinnamate | 6.0 |
| TiO$_2$ | 2.0 |
| Isopropyl Palmitate | 3.0 |
| Paraffin Soft White | 1.0 |
| Phenyl Trimethicone | 2.0 |
| Light Liquid Paraffin | 1.0 |
| Unilin | 0.5 |
| Cetostearyl Alcohol | 0.5 |
| Glyceryl Stearate/PEG-100 Stearate | 0.5 |
| Stearic Acid | 0.5 |
| Propylparaben | 0.05 |
| Imidazolidinyl Urea | 0.2 |
| Methylparaben | 0.15 |
| | 100.0 |

The composition of Table 8 remained stable after two months at 4° C., 30° C., 40° C. and 50° C.

EXAMPLE 8

The composition of Table 9 was prepared according to the following method.

Carbomer 941 and Keltrol F (xanthan gum) were mixed and added to water in which disodium EDTA was dissolved. Triethanolamine was added until the pH was between pH 8.0 and 9.0. Glycerine, PPG-20 methyl glucose ether distearate, imidazolidinyl urea and methyl paraben were added and the mixture was heated to 80°–85° C.

The oil phase ingredients were combined: paraffin soft white, phenyl trimethicone, light liquid paraffin, cetostearyl alcohol, sunscreen actives, glyceryl stearate/PEG-100 stearate (Arlacel 165), stearic acid, Unilin and propyl paraben. The mixture was then heated to 80°–85° C.

Isopropyl palmitate and microfine titanium dioxide were mixed to a smooth paste and added to the heated oil phase. Potassium cetyl phosphate was added to the heated oil phase and dissolved. The oil phase was then reheated to 80°–85° C.

The heated oil phase was added to the heated water phase and the mixture was homogenized and cooled to 40°–45° C. Fragrance was added (if required).

TABLE 9

| Raw Materials | Weight % |
| --- | --- |
| Water | 74.18 |
| Xanthan Gum | 0.1 |
| Carbomer 941 | 0.3 |
| EDTA (disodium salt) | 0.02 |
| Triethanolamine | 0.5 |
| Glycerine | 0.5 |
| PPG-20 Methyl Glucose Ether Distearate | 2.0 |
| Potassium Cetyl Phosphate | 1.0 |
| Oxybenzone | 2.0 |
| Octyl Methoxycinnamate | 7.5 |
| TiO$_2$ | 2.0 |
| Isopropyl Palmitate | 3.0 |
| Paraffin Soft White | 1.0 |
| Phenyl Trimethicone | 2.0 |
| Light Liquid Paraffin | 1.0 |
| Unilin | 1.0 |
| Cetostearyl Alcohol | 0.5 |
| Glyceryl Stearate/PEG-100 Stearate | 0.5 |
| Stearic Acid | 0.5 |
| Propylparaben | 0.05 |
| Imidazolidinyl urea | 0.2 |
| Methylparaben | 0.15 |
| | 100.0 |

The emulsion of Table 9 remained stable after three months at 4° C., 30° C., 40° C. and 50° C.

EXAMPLE 9

The composition of Table 10 was prepared according to the following procedure.

Carbomer 941 and Keltrol F (xanthan gum) were mixed and added to water in which disodium EDTA was dissolved. Triethanolamine was added until the pH was between pH 8.0 and 9.0. Glycerine, PPG-20 methyl glucose ether, imidazolidinyl urea and methyl paraben were added and the mixture was heated to 80°–85° C.

The oil phase ingredients were combined: paraffin soft white phenyl trimethicone, light liquid paraffin, cetostearyl alcohol, sunscreen actives, glyceryl stearate/PEG-100 stearate (Arlacel 165), stearic acid, Unilin and propyl paraben. The mixture was then heated to 80°–85° C.

Isopropyl palmitate and microfine titanium dioxide were mixed to a smooth paste and added to the heated oil phase. Potassium cetyl phosphate was added to the heated oil phase and dissolved. The oil phase was then reheated to 80°–85° C.

The heated oil phase was added to the heated water phase and the mixture was homogenized and cooled to 40°–45° C. Fragrance was added (if required).

TABLE 10

| Raw Materials | Weight % |
| --- | --- |
| Water | 74.88 |
| Xanthan Gum | 0.1 |
| Carbomer 941 | 0.2 |
| EDTA (Disodium salt) | 0.02 |
| Triethanolamine | 0.4 |
| Glycerine | 0.5 |
| PPG-20 Methyl Glucose Ether Distearate | 2.0 |
| Potassium Cetyl Phosphate | 1.0 |
| Oxybenzone | 2.0 |
| Octyl Methoxycinnamate | 7.5 |
| TiO$_2$ | 2.0 |
| Isopropyl Palmitate | 3.0 |
| Paraffin Soft White | 1.0 |
| Phenyl Trimethicone | 2.0 |
| Light Liquid Paraffin | 1.0 |
| Unilin | 0.5 |
| Cetostearyl Alcohol | 0.5 |
| Glyceryl Stearate/PEG-100 Stearate | 0.5 |
| Stearic Acid | 0.5 |
| Propylparaben | 0.05 |
| Imidazolidinyl Urea | 0.2 |
| Methylparaben | 0.15 |
| | 100.0 |

The composition of Table 10 remained stable after three months at 4° C., 30° C., 40° C. and 50° C.

We claim:

1. A sunscreen composition in oil-in-water emulsion form having cosmetically acceptable properties and having substantially uniformly suspended therein from about 0.5% to about 5%, by weight, of microfine $TiO_2$ having a particle size of less than about 100 nm, said composition further comprising a dispersing agent in an amount sufficient to stabilize said emulsion, said dispersing agent comprising a long chain saturated primary alcohol, having an average of from about 25 to about 45 carbon atoms in the long chain, ethoxylated or unethoxylated.

2. The sunscreen composition of claim 1 in cream form.

3. The sunscreen composition of claim 1 in lotion form.

4. The sunscreen composition of claim 1 wherein said dispersing agent is present in an amount in the range of from about 0.2 to about 10%, by weight, based on the weight of said composition.

5. The sunscreen composition of claim 1 wherein the long chain has carbon atoms average of from about 30 to 40.

6. The sunscreen composition of claim 1 wherein the titanium dioxide minimum is at least 1 wt. %.

7. The sunscreen composition of claim 1 wherein the minimum titanium dioxide is 2 wt. %.

* * * * *